(12) United States Patent
Cheng et al.

(10) Patent No.: US 9,719,955 B2
(45) Date of Patent: Aug. 1, 2017

(54) HEMATOCRIT MEASUREMENT SYSTEM AND MEASUREMENT METHOD USING THE SAME

(71) Applicant: Apex Biotechnology Corp., Hsinchu (TW)

(72) Inventors: Chu-Ming Cheng, Hsinchu (TW); Lee Teng Yi Wu, Hsinchu (TW); Ching-Yuan Chu, Hsinchu (TW)

(73) Assignee: Apex Biotechnology Corp., Hsinchu (TW)

( * ) Notice: Subject to any disclaimer, the term of this patent is extended or adjusted under 35 U.S.C. 154(b) by 444 days.

(21) Appl. No.: 14/486,869

(22) Filed: Sep. 15, 2014

(65) Prior Publication Data

US 2015/0136617 A1 May 21, 2015

(30) Foreign Application Priority Data

Nov. 19, 2013 (TW) .............................. 102142018 A

(51) Int. Cl.
*G01N 27/327* (2006.01)

(52) U.S. Cl.
CPC ....... *G01N 27/327* (2013.01); *G01N 27/3274* (2013.01)

(58) Field of Classification Search
CPC .......................... G01N 27/327; G01N 27/3274
USPC ...................................... 205/792; 204/403.02
See application file for complete search history.

(56) References Cited

U.S. PATENT DOCUMENTS 5,628,890 A 5/1997 Carter et al.
7,407,811 B2 8/2008 Burke et al.

8,480,869 B2 7/2013 Fujiwara et al.
2002/0135385 A1 9/2002 Magill
2008/0211521 A1 9/2008 Lock
2011/0309846 A1 12/2011 Elder et al.
(Continued)

FOREIGN PATENT DOCUMENTS

EP 0417796 A2 3/1991
EP 2120042 A1 11/2009
(Continued)

OTHER PUBLICATIONS

Trebbels et al., A high precision on-line measurement system based on impedance spectroscopy for use in hemodialysis machines, IFMBE Proceedings, 25/VII, pp. 247-250 (2009).*
(Continued)

*Primary Examiner* — Jayne Mershon
(74) *Attorney, Agent, or Firm* — Snell & Wilmer L.L.P.

(57) ABSTRACT

A hematocrit (HCT) measurement system and measurement method using the same are disclosed. The hematocrit (HCT) measurement system comprises a test strip and a measurement apparatus comprising: a connector transmitting an initial signal generated from a blood sample to the measurement apparatus, a capacitive reactance adjustor disposed between the test strip and the measurement apparatus, a calculation unit for calculating concentration and HCT value of the blood sample, an A/D convertor transforming the corresponding initial signal to a digital signal, and a signal processor processing the digital reacted signal and showing measured results on a display, wherein the HCT value is calculated by voltage partition to prevent the signal waveform voltage being saturated or cutoff, thereby resulting in measured signal distortion.

15 Claims, 13 Drawing Sheets

(56) References Cited

U.S. PATENT DOCUMENTS

2013/0084589 A1* 4/2013 Kraft ................ G01N 27/3273
                                                    435/14
2013/0175814 A1* 7/2013 Pedersen ................ F03D 1/001
                                                    294/67.5

FOREIGN PATENT DOCUMENTS

| TW | M343160 U   | 10/2008 |
|----|-------------|---------|
| TW | M346003 U   | 12/2008 |
| TW | 200925594 A | 6/2009  |
| TW | M359696 U1  | 6/2009  |
| TW | M362992 U   | 8/2009  |
| TW | 201009331 A | 3/2010  |
| TW | M375871 U1  | 3/2010  |
| TW | 201109656 A1| 3/2011  |
| TW | 201116821 A1| 5/2011  |
| TW | 201132975 A1| 10/2011 |
| TW | 201202705 A1| 1/2012  |

OTHER PUBLICATIONS

EPO; Search Report mailed Mar. 31, 2015 in counterpart European Application No. 14003223.6.

TIPO; Notice of Examination Opinion mailed Jan. 6, 2015 in counterpart Taiwanese Application No. 102142018.

TIPO; Search Report mailed Jan. 6, 2015 in counterpart Taiwanese Application No. 102142018.

* cited by examiner

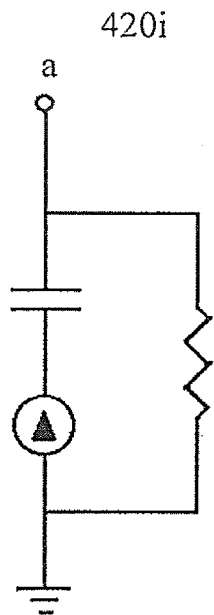
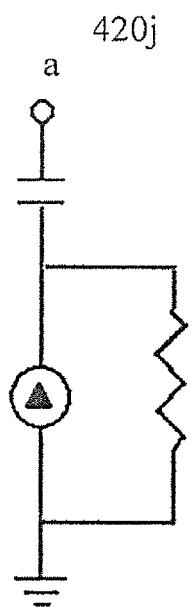
FIG.6i        FIG.6j
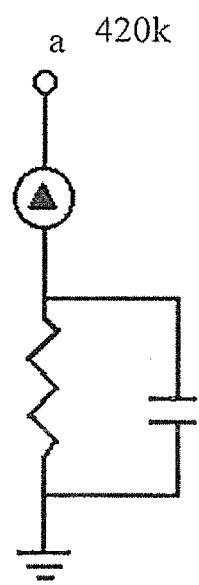
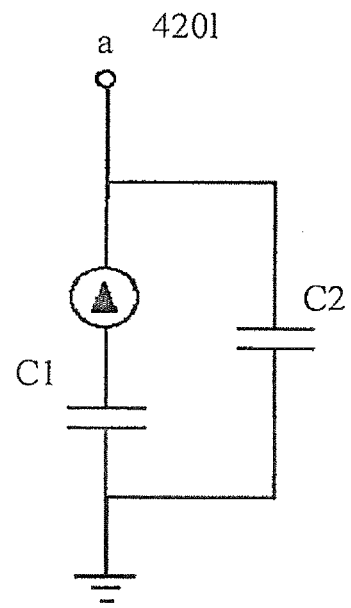
FIG.6k        FIG.6l

HEMATOCRIT MEASUREMENT SYSTEM AND MEASUREMENT METHOD USING THE SAME

CROSS-REFERENCE TO RELATED APPLICATIONS

This application claims the right of priority based on Taiwanese Patent Application No. 102142018 entitled "Hematocrit Measurement System and Measurement Method Using the Same," filed on Nov. 19, 2013, which is incorporated herein by reference and assigned to the same assignee herein.

FIELD OF THE INVENTION

The present invention relates to a hematocrit measurement system and a measurement method thereof, and more particularly to a hematocrit measurement system having a capacitive reactance adjustor and a method of improving capacitive reactance characteristics of the blood hematocrit using the capacitive reactance adjustor so as to enhance measurement accuracy.

BACKGROUND OF THE INVENTION

In view of improper eating habits in the modern rich life, diet-caused diseases are increasing. Bioelectrochemical measurement systems with high reliable accuracy for those who require long-term monitoring health status (such as glucose, lipids, etc.) have gradually become an indispensable tool for life.

Conventional electrochemical and biochemical measurement systems may present significant errors for measurement results. That is because blood composition includes interference components to the measurement results. The most representative interference components that interfere are the proportion of red blood cells in the blood (i.e., hematocrit, hereinafter referred to as HCT). The blood HCT is an important parameter leading to occurrence of errors in measurement results. For example, in operating measurements of blood glucose, cholesterol, uric acid and blood clotting speed, red blood cells may impede reaction between the blood and an enzyme, causing the measurement result of high HCT presented lower than its actual value, while the measurement result of low HCT presented higher than its actual value.

With reference to current background art, there are a variety of technical solutions to solve the problems caused by HCT. For example, U.S. Pat. No. 5,628,890, the entity of which is incorporated herein by reference, discloses a test strip for an electrochemical system. A filter layer is disposed on the test strip to separate the red blood cells from the blood sample to be tested. However, the method disclosed in this patent has drawbacks such as difficulty to process the test strip, high cost, long measurement time taken, and large amount of measurement blood needed.

U.S. Pat. No. 7,407,811 discloses a method for detecting HCT and correcting the concentration of the blood to be tested. AC signals with frequencies in a range of 1 Hz-20 KHz are provided to test the blood sample. The phase angle and admittance magnitude of the blood can be measured and HCT values in the blood can be calculated therefrom. However, the technical solutions disclosed in this patent need repeated providing of two to five signals with different frequencies to the tested blood. It is a practical disadvantage that the blood HCT is measured by signals with different frequencies, resulting in long overall reaction time, operational difficulties, and increased power consumption.

In addition, U.S. Pat. No. 8,480,869 discloses an HCT measurement method using a redox reaction in which ferricyanide or ferrocyanide is disposed on electrochemical test strip electrodes. After ferricyanide or ferrocyanide reacts with red blood cells, the HCT value can thereby be measured. However, the redox agents disclosed in U.S. Pat. No. 8,480,869 may interfere with other enzymes on the electrochemical test strip, resulting in a distortion of the measurement results. Further, although both U.S. Pat. Nos. 7,407,811 and 8,480,869 disclose methods to measure HCT values of the blood, other components in the blood can also pose a threat to the accuracy of HCT measurement. Moreover, although U.S. Pat. No. 5,628,890 discloses that the red blood cells can be separated from the blood for testing, the presence of HCT cannot be completely filtered out. Accordingly, HCT measurement systems with high accuracy and reliability are needed for the industry based on overcoming the above disadvantages of conventional technologies.

SUMMARY OF THE INVENTION

One aspect of the present invention provides an HCT measurement system, comprising an electrochemical test strip and a measuring instrument, wherein blood HCT capacitance characteristics and measurement accuracy can thus be effectively improved using a blood measuring instrument with a capacitive reactance characteristic adjustor.

The a measurement apparatus comprises: a power generator providing a signal; a connector transmitting an initial signal generated from a blood sample to the measurement apparatus; a capacitive reactance adjustor disposed between the test strip and the measurement apparatus; a calculation unit for calculating concentration and HCT value of the blood sample; an A/D convertor transforming the corresponding initial signal to a digital reacted signal; and a signal processor processing the digital signal and showing measured results on a display, wherein the calculation unit measures the signal to calculate the HCT value of the blood sample such that distortion measurement signal curves due to saturated or cut off signal waveform voltage is prevented.

According to an embodiment of the invention, the adjusting capacitor of the signal processor and a capacitance of the blood sample present a parallel relationship, wherein an overall circuitry capacitance $C_{eq}$ of the signal processor satisfies the following equation:

$$C_{eq}=C_b+C_{ac},$$

where $C_{eq}$ is the overall circuitry capacitance, $C_b$ is the capacitance of the blood sample, and $C_{ac}$ is the adjusting capacitance, thereby amplifying the measurement signal and achieving effects of reducing the required amount of blood.

According to another embodiment of the invention, the adjusting capacitor of the signal processor and a capacitance of the blood sample present a serial relationship, wherein an overall circuitry capacitance $C_{eq}$ of the signal processor satisfies the following equation:

$$1/C_{eq}=1/C_b+1/C_{ac},$$

where $C_{eq}$ is the overall circuitry capacitance, $C_b$ is the capacitance of the blood sample, and $C_{ac}$ is the adjusting capacitance, thereby effectively filtering interference signals.

Further, the calculation unit measures a voltage division signal to calculate the HCT value of the blood sample such that distortion measurement signal curves due to saturated or cut off signal waveform voltage can be prevented.

According to another embodiment of the invention, a method for measuring hematocrit (HCT) using an HCT measurement system comprises: providing an electrochemical test strip; placing the electrochemical test strip into the HCT measurement system (e.g., as set forth herein); providing a wave function signal to the electrochemical test strip transmitted from a power generator to the connector and the capacitive reactance adjustor; acquiring a measuring signal through the calculation unit; analyzing the measuring signal through the signal processor; and showing a measured HCT value on a display through the signal processor or using the HCT value to calculate concentration of other compositions of sample.

BRIEF DESCRIPTION OF THE DRAWINGS

The foregoing aspects and many of the attendant advantages of this invention will become more readily appreciated by reference to the following detailed description, when taken in conjunction with the accompanying pictures, wherein.

DETAILED DESCRIPTION OF THE INVENTION

Figure 1:
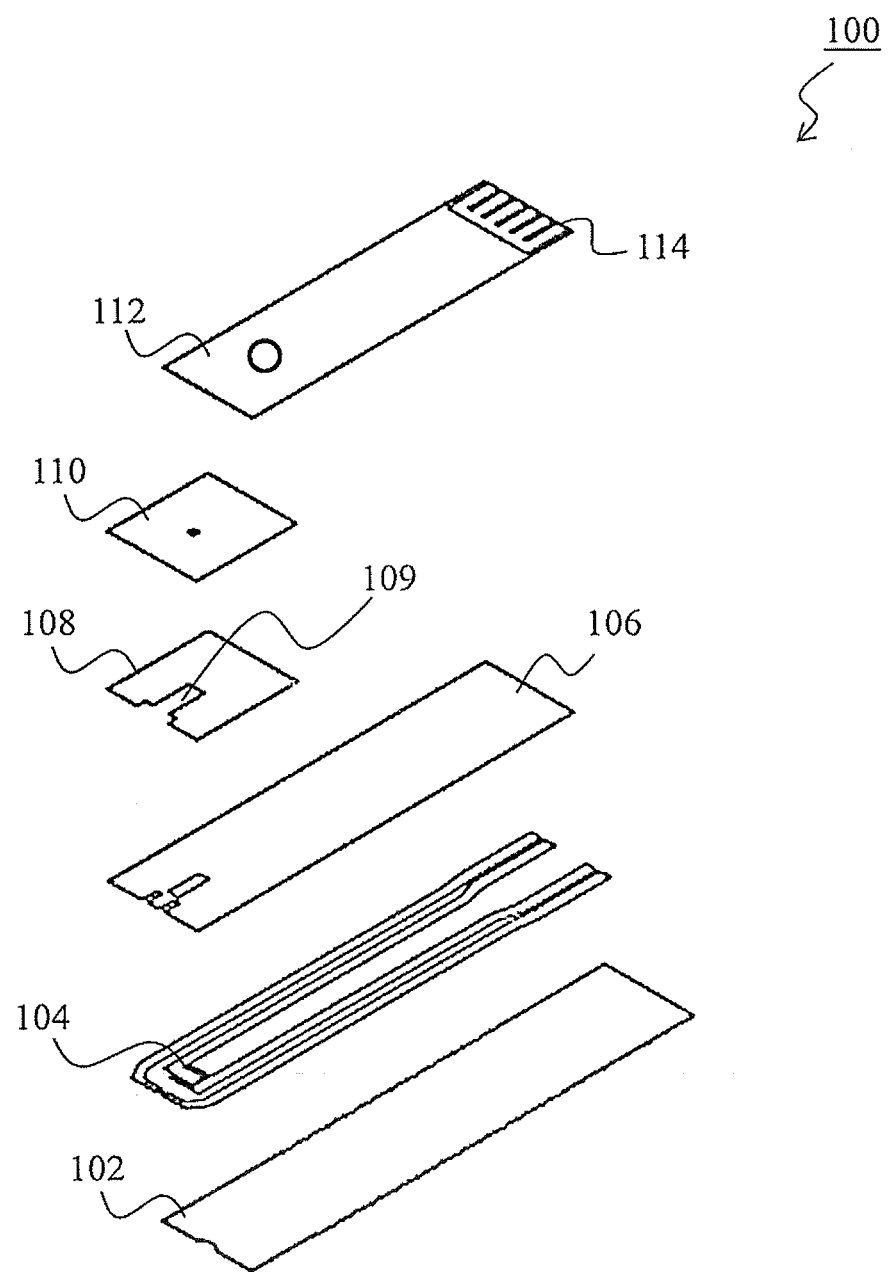
FIG. 1 illustrates an exploded view schematically showing the structure of the electrochemical test strip according to an embodiment of the invention.

Reference will now be made in detail to several exemplary embodiments of the invention, examples of which are illustrated in the accompanying drawings. Wherever possible, the same reference numbers are used in the drawings and the description to refer to the same or like parts. In the drawings, the shape and thickness of an embodiment may be exaggerated for clarity and convenience. Note that the features illustrated in the drawings are not necessarily drawn to scale. Descriptions of well-known components, materials, and process techniques may be omitted so as to not unnecessarily obscure the embodiments of the invention. Any devices, components, materials, and steps described in the embodiments are only for illustration and not intended to limit the scope of the present invention.

Embodiments of the present invention provide a method for measuring blood HCT using a biochemical system. The biochemical system comprises a measurement apparatus and an electrochemical test strip, wherein the electrochemical test strip includes at least one pair of electrodes. When operating the measurement apparatus, the users insert the electrochemical test strip into the measurement apparatus. A patient's skin is then pricked using a blood collection needle to ooze trace blood, which is directly dripped onto the electrochemical test strip. When the blood is dripped and sucked into the reaction layer on the top of the electrode, HCT concentration can be measured by measuring the resistance and capacitance of the blood. That is because the red blood cells in the blood include capacitive and resistance characteristics in structure such that there is a direct relationship between use of the capacitive and reactance characteristics and the HCT concentration.

FIG. 1 illustrates an exploded view schematically showing the structure of the electrochemical test strip according to an embodiment of the invention. Referring to FIG. 1, an electrochemical test strip 100 includes an insulating substrate 102, an electrode system 104, an insulating layer 106, a lower separation plate 108, a hydrophilic separation plate 110 and an upper separation plate 112. The insulating substrate 102 is an electrically insulating substrate, and its material may include, but is not limited to: polyvinyl chloride (PVC), glass fiber, polyester, bakelite, polyethylene terephthalate (PET), poly carbonate esters (PC), polypropylene (PP), polyethylene (PE), polystyrene (PS), ceramic or any combination thereof.

Materials of the electrode system 104 may include any conductive material, such as carbon plastic, silver plastic, copper, rubber, gold and silver mixed glue, carbon silver mixed glue, or any combination thereof. In one embodiment, the electrode system is composed of a carbon powder conductive layer. In another embodiment, the electrode system is composed of a metal layer. In further another embodiment, the electrode system is composed of a silver-based conductive layer and a carbon powder conductive layer located thereon, wherein impedance of the carbon powder conductive layer is typically much greater than that of the silver-based conductive layer or other metal layer. Further, according to embodiments of the invention, in response to the actual needs in measurement, the electrode system can be a set of electrodes consisting of a plurality of electrodes insulated from each other. In the present embodiment, the electrode system comprises a concentration electrode set and an HCT electrode set. The concentration electrode set comprises a working electrode and a reference electrode insulating from each other. The HCT electrode set comprises a first HCT electrode and a second HCT electrode. In measurement, the working electrode, the reference electrode, the first HCT electrode and the second electrode are electrically connected to a measurement apparatus and a blood sample respectively. Note that the present invention does not intend to limit the configuration of the electrodes, as long as an electrical circuit can be formed between the electrode set and the measurement apparatus. Generally, it would be sufficient to exploit the present invention as long as each electrode of the aforementioned electrode configuration is insulated from each other before connecting the blood sample. Embodiments of the present invention are not intended to be limited by the arrangement between the electrodes and are not intended to be limited by the number of electrodes; other electrodes may be added depending on the practical application.

The insulating layer 106 covers part of the electrode system 104 so that a reaction zone for receiving a blood sample is formed at one end of the electrode system 104 not covered while the other end forms a connection area in contact with the measurement apparatus, wherein the reaction zone includes an inlet for injecting the blood sample. Materials of the insulating layer 106 can include, but are not limited to a PVC insulating tape, a PET insulating tape, a thermal drying insulating paint or an ultraviolet drying insulating paint. According to one embodiment of the invention, the electrochemical test strip 100 may include at least one reaction layer disposed in the reaction zone. The reaction layer contains at least one oxidoreductase to produce a chemical reaction with the blood sample, wherein the type of oxidoreductase is determined depending on the nature of the blood sample. Further, the reaction layer covers at least part of the reaction zone of the electrode system.

The lower separation plate 108 is disposed over the insulating layer 106, and the lower separation plate 108 includes an opening 109 exposing a portion of the electrode system. Generally, it would be sufficient to implement as long as the opening 109 exposed part of the electrode system. The present invention does not intend to limit the shape of the opening 109. Further, the connecting region of the insulating substrate 102 is exposed by the lower separation plate 108 such that one end of the connection area of the electrode system electrically connects the measurement apparatus. Materials of the lower separation plate 108 can include, but are not limited to a PVC insulating tape, a PET insulation tape, a thermal drying insulating paint or an UV curable insulating paint. Furthermore, during the manufacturing process of the lower separation plate 108, the lower separation plate with the trimmed opening can be placed on the insulating substrate and the electrode system. Alternatively, the lower spacer can be formed on part of the insulating substrate and the electrode system by directly printing and selectively avoiding the opening 109 and the position of the connection region of the insulating substrate.

Materials of the upper separation plate 112 can include, but are not limited to transparent or translucent material so as to easily observe whether the reaction zone is filled with the blood sample and to avoid testing with the blood sample unfilled, resulting in erroneous measurements. The lower surface of the upper separation plate 112 near the reaction zone can be coated with a hydrophilic spacer 110 to enhance capillary action on the internal walls of the reaction zone and more rapidly and efficiently introduce the blood sample into the reaction zone. The upper separation plate 112 further comprises a vent hole corresponding to the openings (not shown) to enhance capillary action, exhausting gas in the reaction zone. In general, the vent hole is disposed near the end of the inner closed opening. Embodiments of the present invention are not limited to the shape of the vent hole, for example, circular, oval, rectangular, diamond, etc.

In one embodiment, the electrochemical test strip 100 can be provided with an identification unit 114, which is formed on the side of upper surface of the electrode system 104 which is in contact with the measurement apparatus. The identification unit 114 includes a plurality of electrical components. The electrical components can be a variety of electrically conductive elements such as electrical elements having electrical characteristics of passive components. In one embodiment, the electrical element can be a resistor which is the same as the material of the electrode system 104. The electrical element can be formed by screen printing, imprinting, thermal transfer printing, spin coating, ink-jet printing, laser ablation, deposition, electroplating, or screen-printing. In another embodiment, the electrical device comprised in the identification unit 114 may include resistors, capacitors, inductors, and/or combinations thereof.

When the identification unit 114 is inserted in a measurement device, the measurement device can identify the location and quantity of each electrical component on the electrochemical test strip 100 meter, thereby identifying the kind of the electrochemical test strip 100 and further adopting corresponding correction parameters or measurement modes. In other words, the number and location of a plurality of electrical components determine an identification code of the electrochemical test strip 100 so that the measurement apparatus can accordingly identify electrochemical test strip 100. The present invention does not intend to limit the number, shape or configuration of the electrical elements comprised in the identification unit 114. The present invention does not intend to limit the location or operating mode of identification unit 114. The only implement criteria for the identification unit 114 is that the identification code can be read by the measurement apparatus. Additional identification units alternatively implemented are disclosed in other Taiwanese patent applications filed by the same applicant including Taiwanese Application Nos. 096146711, 097202289, 097208206, 097207619, 097133258, 098202095, 098131024, 098215494 and 099144438, the entirety of the abovementioned applications are incorporated herein by reference.

FIGS. 2a-2d schematically show layouts of the electrode system according to some embodiments of the present invention. Referring to FIGS. 2a-2d respectively, fulfilling the measurement requirements, an electrode system including a plurality of sets of electrodes is disposed on a single electrochemical test strip. According to embodiments of the present invention, the electrode system includes but is not limited to a concentration electrode set and an HCT electrode set. The concentration-electrode set includes at least one working electrode W and a reference electrode C. HCT measurement does not contain redox reaction. Since a signal waveform is provided by the measurement apparatus in the blood, the HCT response signal can be measured therefrom. The HCT electrode set for measuring HCT is composed of a first HCT electrode H1 and a second HCT electrode H2.

Figure 2A:
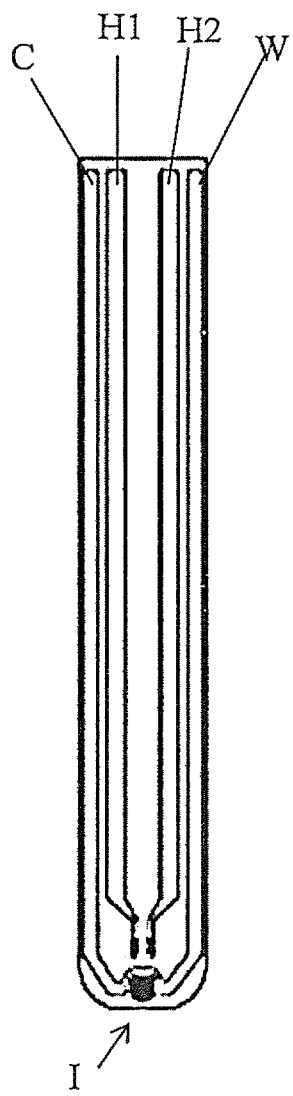
FIGS. 2a-2d schematically show layouts of electrode systems according to embodiments of the present invention.
Figure 2B:
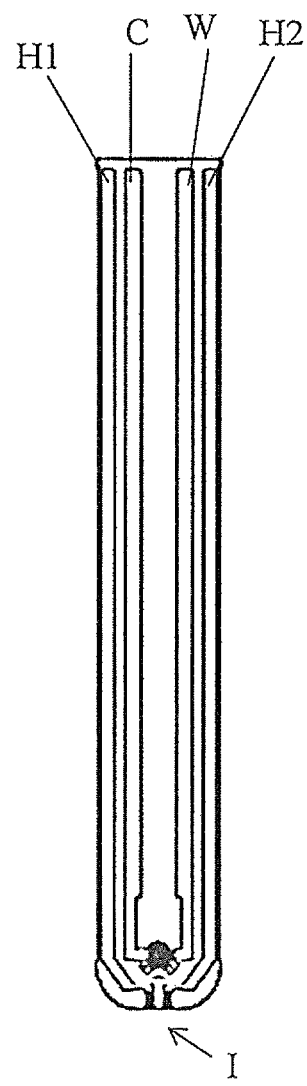
Figure 2C:
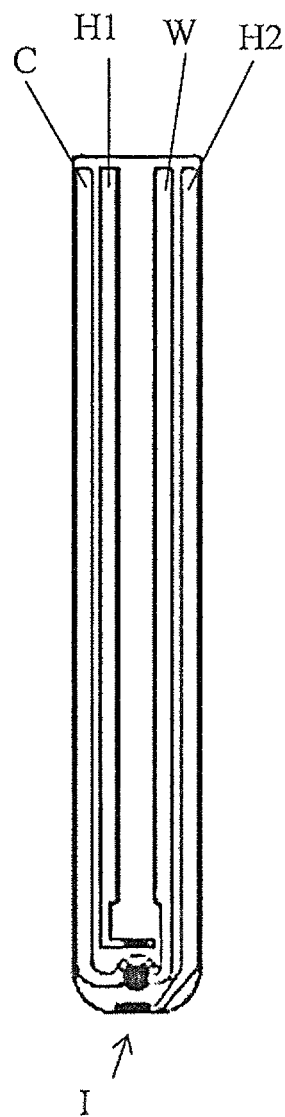
Figure 2D:
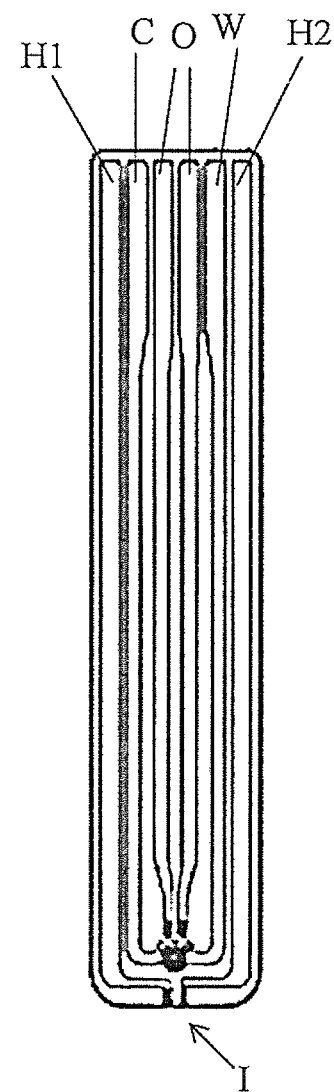

According to embodiments of the present invention, arrangement of each electrode set is not particularly limited. When the blood sample infuses into entrance I of the reaction zone, it comes into contact with the HCT electrode set and the concentration electrode set of the electrode system sequentially. Note that the entrance sequence of the blood samples contacting electrodes of the reaction zone is not limited, and the electrode sets can be adjusted according to actual required measurement position, if only one electric loop can be formed between the electrode set and the blood sample, thus sufficiently implementing measurement embodiments of the invention. In one embodiment, configuration of the electrode set of the electrochemical test strip is shown in FIG. 2a. Working electrode W and reference electrode C of the concentration electrode set are set up closer to the entrance I of the blood sample than the HCT electrode set. In another embodiment, an alternative configuration of the electrode set of the electrochemical test strip is shown in FIG. 2b. The first HCT electrode H1 and the second HCT electrode H2 of the HCT electrode set are set up closer to the entrance I of the blood sample than the concentration electrode set. In a further embodiment, an alternative configuration of the electrode set of the electrochemical test strip is shown in FIG. 2c. Working electrode W and reference electrode C of the concentration electrode set are set up between the first HCT electrode H1 and the second HCT electrode H2 of the HCT electrode set. Further, configuration of the electrode set of the electrochemical test strip of the present invention can also be shown in FIG. 2d. In addition to the concentration electrode set and the HCT electrode set, there are other electrode sets O included. Note that the present invention does not intent to limit layouts and measuring the relationship between each of the electrode sets. The electrical connection relationship can be adjusted according to actual measurement needs. A single measurement implementation can be individually performed between the electrode sets. More than one measurement implementation can also be performed on the same electrode set. For example, HCT and concentration measurements can be implemented on the same electrode set. Another embodiment of the electrode system may include a ⊓ shape electrode, which is electrically insulated from each measurement electrode. The ⊓ shape electrode is configured to electrically connect with the measurement apparatus. When the electrochemical test strip is inserted into the measurement apparatus, an electrical loop is formed between the ⊓ shape electrode and the measurement apparatus, thereby starting the measurement operation.

For simplification of the specification, the following description is only focused on the HCT measurement. Those skilled in the art, however, can easily combine the HCT measurements disclosed in the invention with other measurements of physiological parameters. For example, the HCT value of the blood sample can be acquired through the HCT measurement method of the present invention, thereby using the HCT value to calculate the biochemical concentration values, which are not limited to glucose, cholesterol, uric acid, lactic acid, and hemoglobin.

When the blood sample flows into the electrochemical test strip, a waveform signal is applied to the reactive layer by the measurement apparatus. After the waveform signal is reacted with the blood sample, an electrical signal will be released, generating a corresponding response signal. By measuring the response signal, the HCT condition of the user can be revealed at the measurement moment.

In the present disclosure, the waveform signal is defined as signals that are stabilized over time and are undulated with circulated current or voltage. The signals can be 100% of AC signals, or the AC and DC superimposed signals, preferably DC signal waveforms. The aforementioned DC waveform signal means when the measurement apparatus provides a signal to the reaction zone of the electrochemical strip, a single signal waveform sufficiently presents characteristics of the waveform, and the waveform characteristic signal does not contain a negative circulated signal. The DC waveform signal can be, but is not limited to a pulse wave, a square wave, a triangle wave or a saw-tooth wave. In the present embodiment, the preferable waveform signal is a square wave signal with frequency approximately in a range of 1 KHz-22 KHz. Voltage is in a range of 50 mV-5 V, preferably in a range of 300 mV-800 mV.

Figure 3:
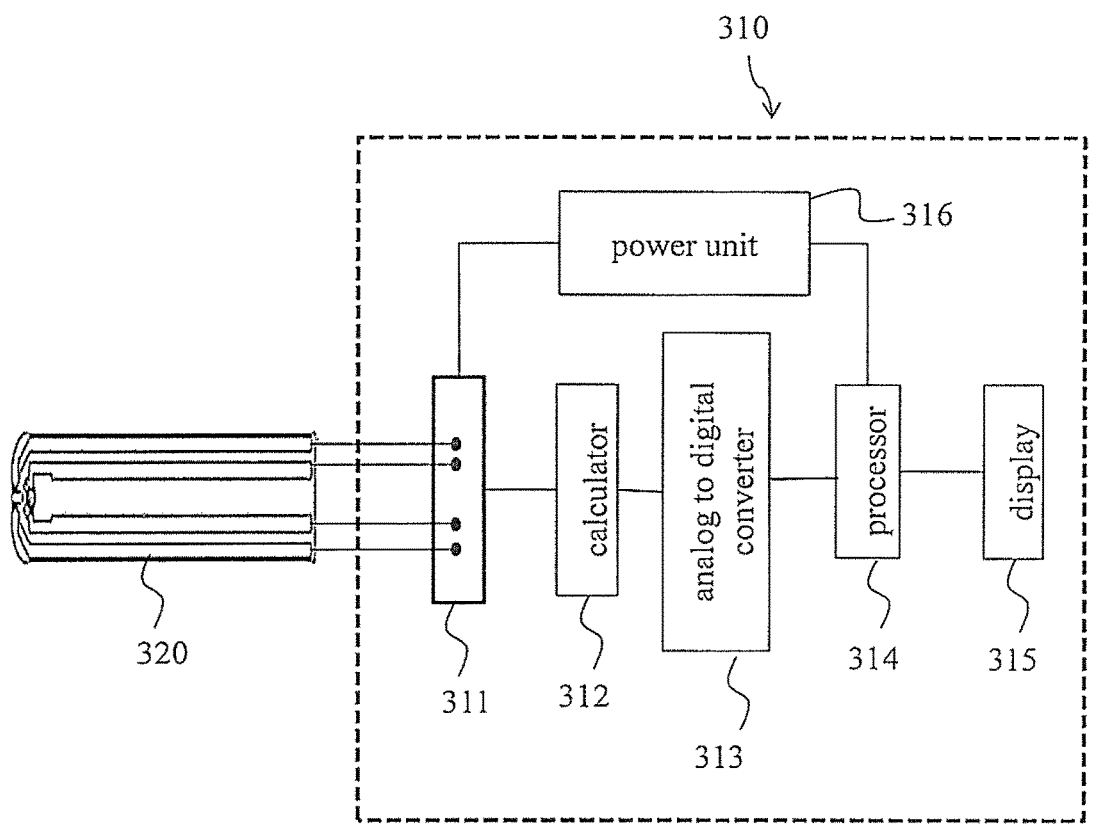
FIG. 3 is a block diagram schematically illustrating a system of the measurement apparatus according to an embodiment of the present invention.

FIG. 3 is a block diagram schematically illustrating a system of the measurement apparatus according to an embodiment of the present invention. The system of the present invention includes an electrochemical test strip 320 and a measurement apparatus 310. The electrochemical test strip 320 comprises a concentration electrode set with a reference electrode C and a working electrode W for concentration measurement, and an HCT electrode set with a first HCT electrode H1 and a second HCT electrode H2 for HCT measurement. The measurement apparatus 310 includes a connector 311 for external connection, a calculator 312 for transforming a concentration and/or HCT value, an analog to digital converter 313, a processor 314 and a display 315. After the blood sample flows into the reaction zone of the electrochemical test strip, the blood sample distributes over the concentration electrode set and the HCT electrode set. When a waveform signal is applied by the power unit 316 to the HCT electrode set, the red blood cells in the blood reacts with an electrical signal to generate a corresponding response signal which is transmitted through the connector 311 to the calculation unit 310 of the measurement apparatus 312. Subsequently, the reaction signal is transformed and transmitted to the analog to digital converter (ADC), to get a digital response signal. The digital response signal is further processed by a processor 314, and/or the measurement results are presented on a display 315.

Figure 4:
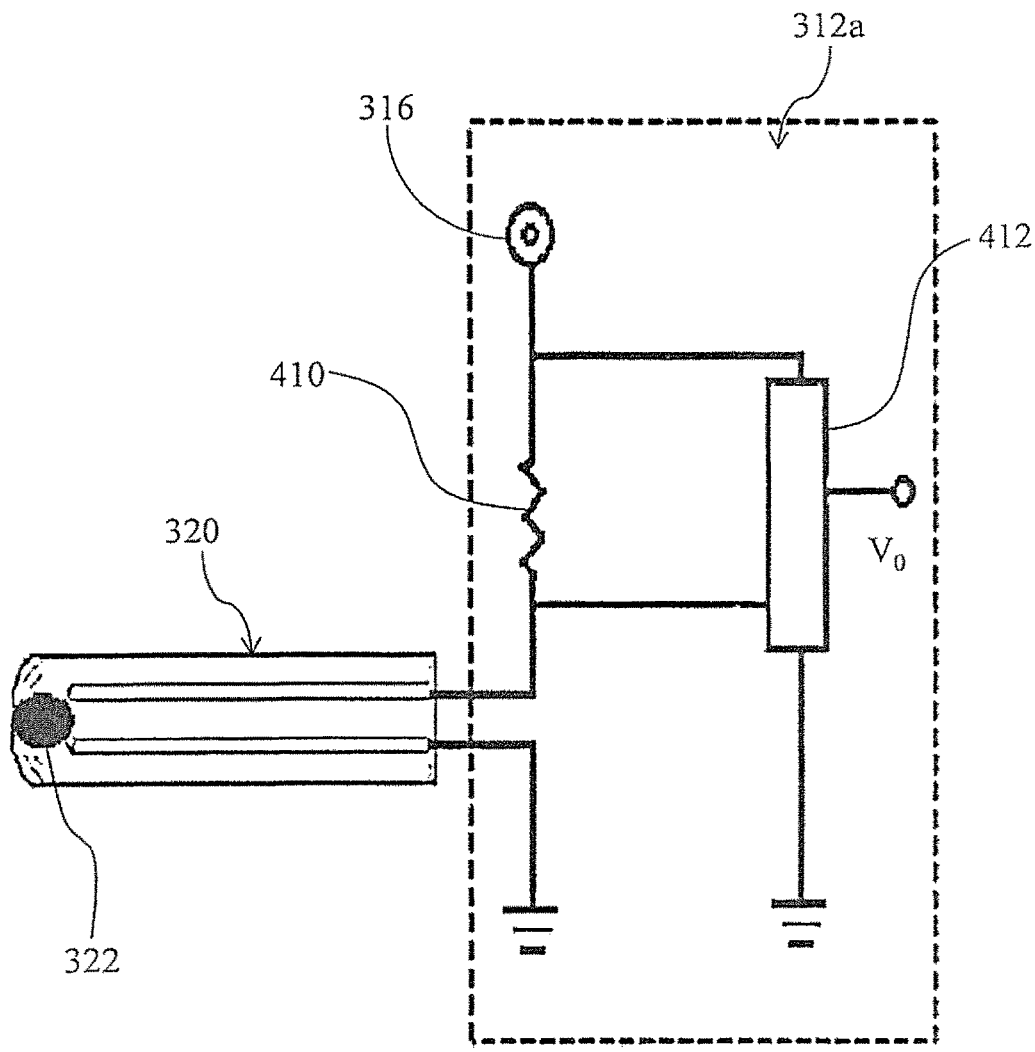
FIG. 4 is an equivalent circuitry of a calculation unit 312a according to an embodiment of the present invention.

FIG. 4 is an equivalent circuitry of a calculation unit 312a according to an embodiment of the present invention. Unlike traditional circuit direct using signal gaining measurement, the calculation unit 312a of the present embodiment adopts voltage division principles to get the blood HCT value. Technical effects such as prevention of measured signal curve distortion caused by signal cut off and/or saturation generated by signal voltage waveform can thus be achieved. The calculation unit 312a is comprised with a divider resistor 410 and signal processor 412. When a waveform signal is provided by the power supply unit 316 through the connector to the blood sample 322, the waveform signal will pass through the divider resistor 410, and the divider resistor 410 and the blood sample 322 are in series relationship. In a series circuit, current through each impedance element is equivalent in accordance with Ohm's law. Since the current through the divided resistor and current through the electrochemical strip with blood sample are the same, measuring the current through the divided resistor can get the current flowing through the blood sample. Further, according to Kirchhoff's voltage law and Ohm's law, the voltage on both ends of each impedance element is equal to the sum of voltage on all components of the circuit. The voltage Vo at signal output terminal satisfies the following relationships:

$$Vo=[R_{SR}/(R_{SR}+R_{BR})]Vs \quad (1)$$

where $R_{SR}$ is impedance of the blood sample, $R_{BR}$ is the divided resistor, and Vs is voltage at the power supply terminal.

According to embodiments of the invention, although there is no restriction on impedance of the divided resistor, it is preferable to not affect measurement of the blood signal by the calculation unit. The impedance is preferably in a range of 200Ω-2 MΩ), more preferably in a range of 2 KΩ-700 KΩ, and further more preferably in a range of 20 KΩ-200 KΩ. Further, the measurement signal is then processed by a signal processor 412. The signal processor 412 can comprise but is not limited to an operational amplifier, an adder, a single integrator or a circuit composed thereof. More preferably, the signal processor is a subtractor.

A lipid bilayer of the red blood cell constitutes an insulating layer. The insulating layer can divide the inner fluid and the outer fluid of the cells, thereby forming a capacitor-like structure. The red blood cells thus have physical characteristics similar to a capacitor. For the household application, the amount of blood samples needed for the measurement system is approximately 15 μL-0.1 μL, or even lower. However, empirical experiment shows that 0.5 μL blood sample contains capacitance of 150 pF-1.5 nF. For conventional electrochemical systems, other components in blood can significantly interfere with the measuring signals, resulting in variation of the measurement results.

In addition, the red blood cell membrane comprises Na+/K+-ATPase. When applying an external electric signal to the blood sample, sodium or potassium ions with electrical signals can be released from the Na+/K+-ATPase due to the potential difference between inside and outside the cell, so as to achieve a potential balance inside and outside the cell. While measuring the HCT value, a signal waveform is provided by the measurement apparatus. Potential in the blood changes as alternately applying the positive and zero potential. Repetitive potential difference between inside and outside the cell causes continuous import and export of sodium or potassium ions from the Na+/K+-ATPase to achieve a potential balance inside and outside the cell. However, the potential difference of the signal is the main course of the noise interference during HCT measurement, further affecting measurement accuracy.

Figure 5:
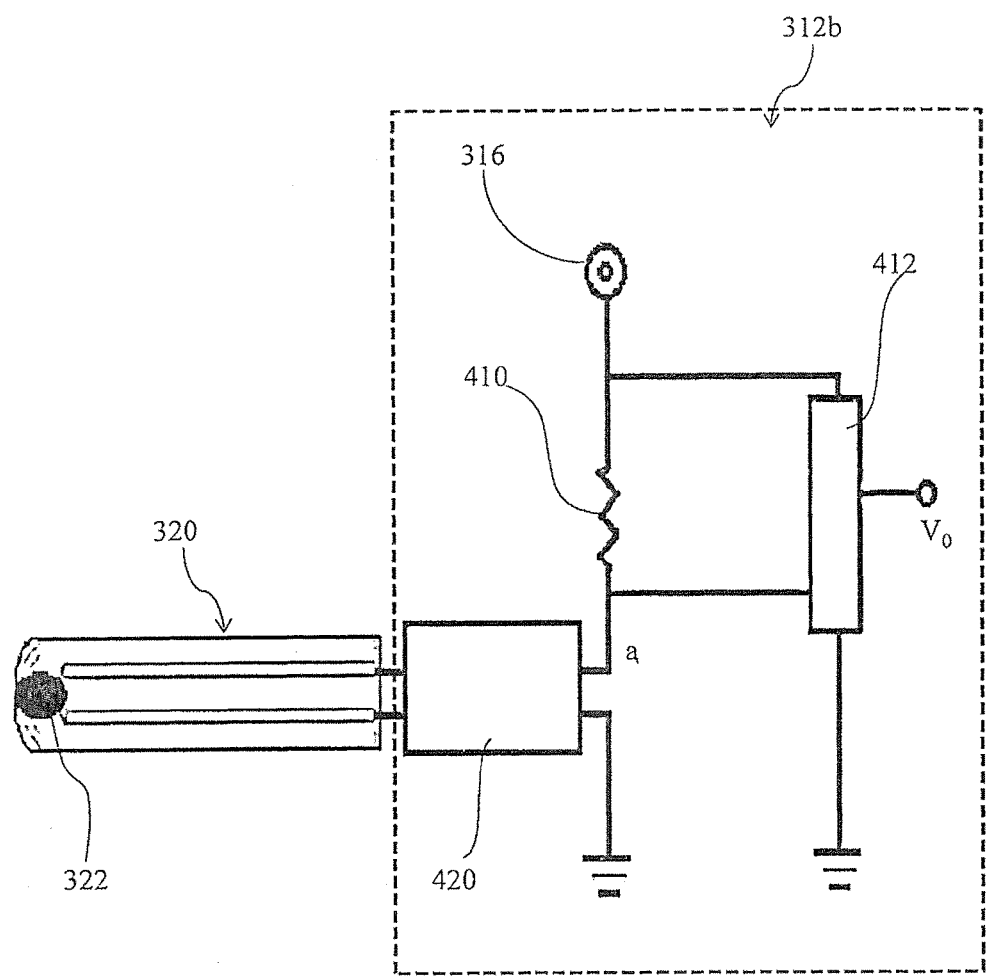
FIG. 5 is an equivalent circuitry of another computing unit 312b according to another embodiment of the present invention.

FIG. 5 is an equivalent circuitry of another computing unit 312b according to another embodiment of the present invention. In order to accurately and precisely detect capacitance characteristics in the blood and improve accuracy of the HCT measurement, a blood capacitance characteristic adjustment device 420 is particularly added in the junction of the electrochemical test strip and the measurement apparatus according to an embodiment of the invention. The capacitance characteristic adjustment device 420 is used to present an electrical connection relationship, thereby improving the capacitance accuracy measured by the measurement apparatus. In addition, since the capacitance characteristic adjustment device 420 can amplify the HCT blood concentration value, the amount of blood sample required for the measurement is apparently reduced.

Figure 6A:
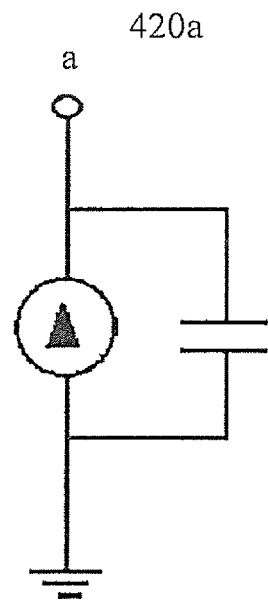
FIGS. 6a-6p show equivalent circuit diagrams of capacitance characteristic adjustment device according to embodiments of the present invention.
Figure 6B:
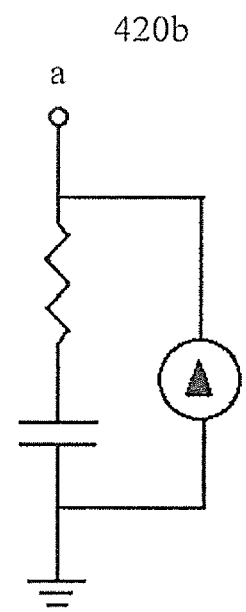
Figure 6C:
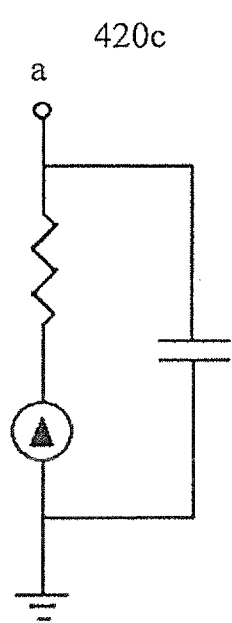
Figure 6D:
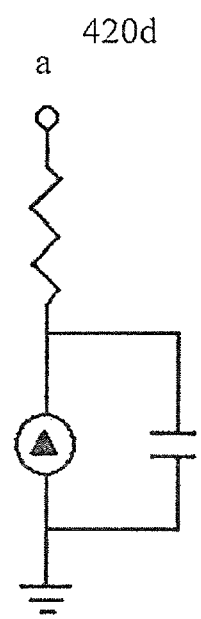
Figure 6E:
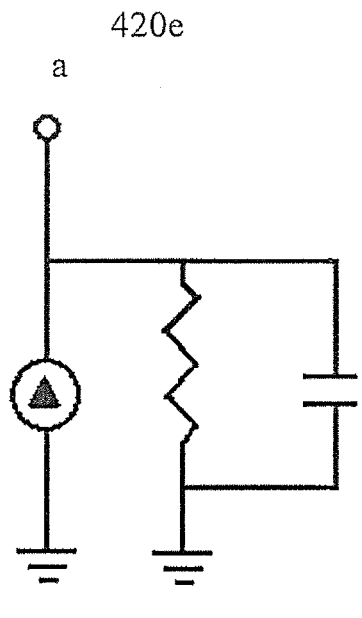
Figure 6F:
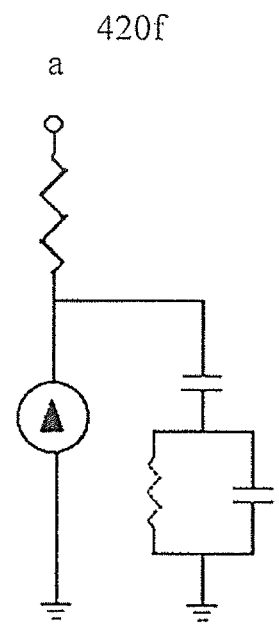
Figure 6G:
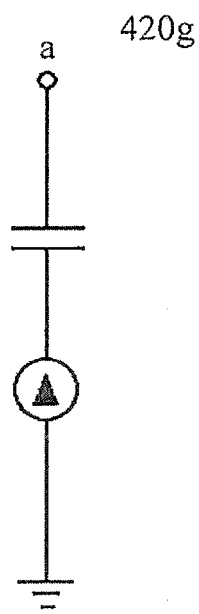
Figure 6H:
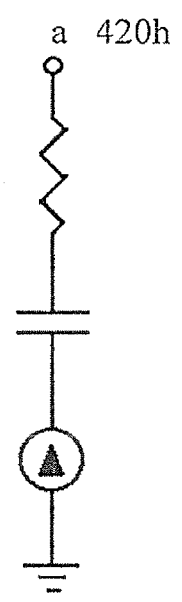
Figure 6M:
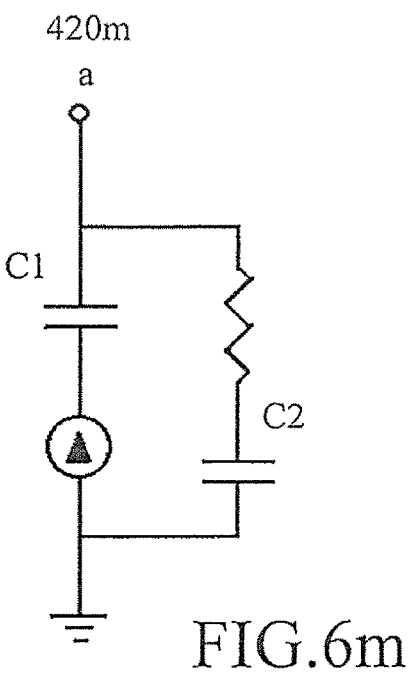
Figure 6N:
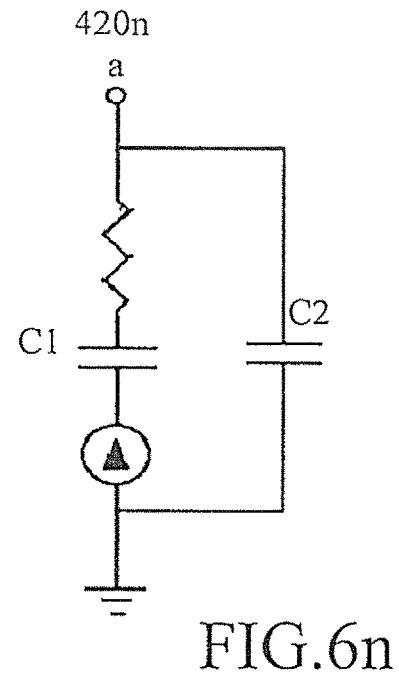
Figure 6O:
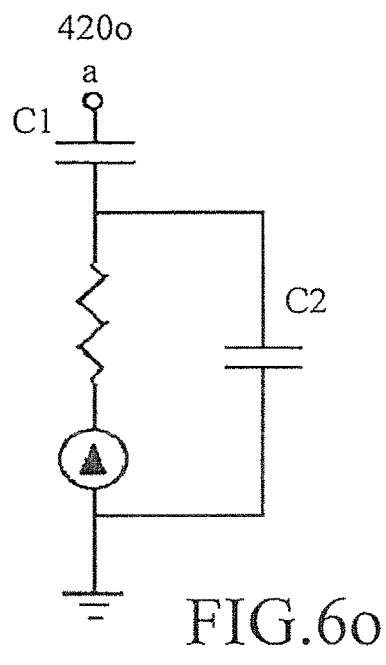
Figure 6P:
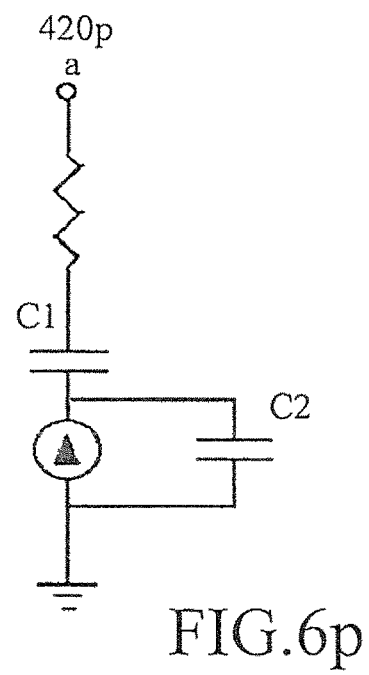

FIGS. 6a-6p show equivalent circuit diagrams of capacitance characteristic adjustment device according to embodiments of the present invention. The capacitance characteristic adjustment device may include, but is not limited to a load resistor and an adjustment capacitance. A junction "a" is created at the electrical connection between a voltage divider resistor and a signal processor. The adjusted capacitance component is composed of a single capacitor or a plurality of capacitive elements. In one embodiment, since a constant of impedance exists in the electrochemical test strip, the loading resistors of FIGS. 6a, 6g and 6l can be substituted by the impedance of the electrochemical test strip.

Further, variation of electrode impedance values for each production batch may exist due to inevitable differences among each batch of material during the manufacturing process of the electrochemical test strip. The loading resistance of the capacitance characteristic adjustment device and the blood sample of the present invention are presented in an electrical connection relationship. The impedance of the electrode can thus directly affect the electrical signals detected by the measurement apparatus. The impedance difference of each batch electrode may result in the difference variation of the electrochemical test strip batch by batch. An identification unit of the electrochemical test strip can thus be used to record the corrected impedance difference of the electrode of each batch. When the electrochemical test strip is inserted into the measurement apparatus, the measurement apparatus reads the corrected impedance difference of the electrode of each batch through the identification unit. The measurement results are corrected by the correction value to avoid measurement errors created by batch-to-batch variation of the electrode impedance difference.

In light of capacitive characteristics of red blood cells in the blood sample, FIGS. 6a-6f show a relation between adjustment capacitance of the capacitance characteristics adjustment capacitor and capacitance of the blood sample which is in a parallel relationship such that the overall circuit capacitance $C_{eq}$ satisfies the following simplified equation:

$$C_{eq}=C_b+C_{ac} \quad (2)$$

where $C_{eq}$ is the overall capacitance of the circuit, $C_b$ is capacitance of the blood sample, an $C_{ac}$ is the adjustment capacitance.

The object of arranging the blood sample in parallel with the adjusted capacitor is to increase stored energy of the capacitance characteristics in the overall circuit, to increase the capacitance value of the overall circuit, and to improve sensitivity to the HCT characteristic signal. Further, arranging the adjustment capacitor in parallel can stabilize voltage and filter the Na+/K+-ATPase and measurement noises caused by other components in the blood. Measurement accuracy can also be improved such that calculation circuit can precisely calculate the capacitance characteristics of blood. In addition, reaction signal can be amplified by arranging the adjustment capacitance in parallel, thereby reducing the amount of blood samples needed to achieve the purpose of minimized detection.

Figure 7:
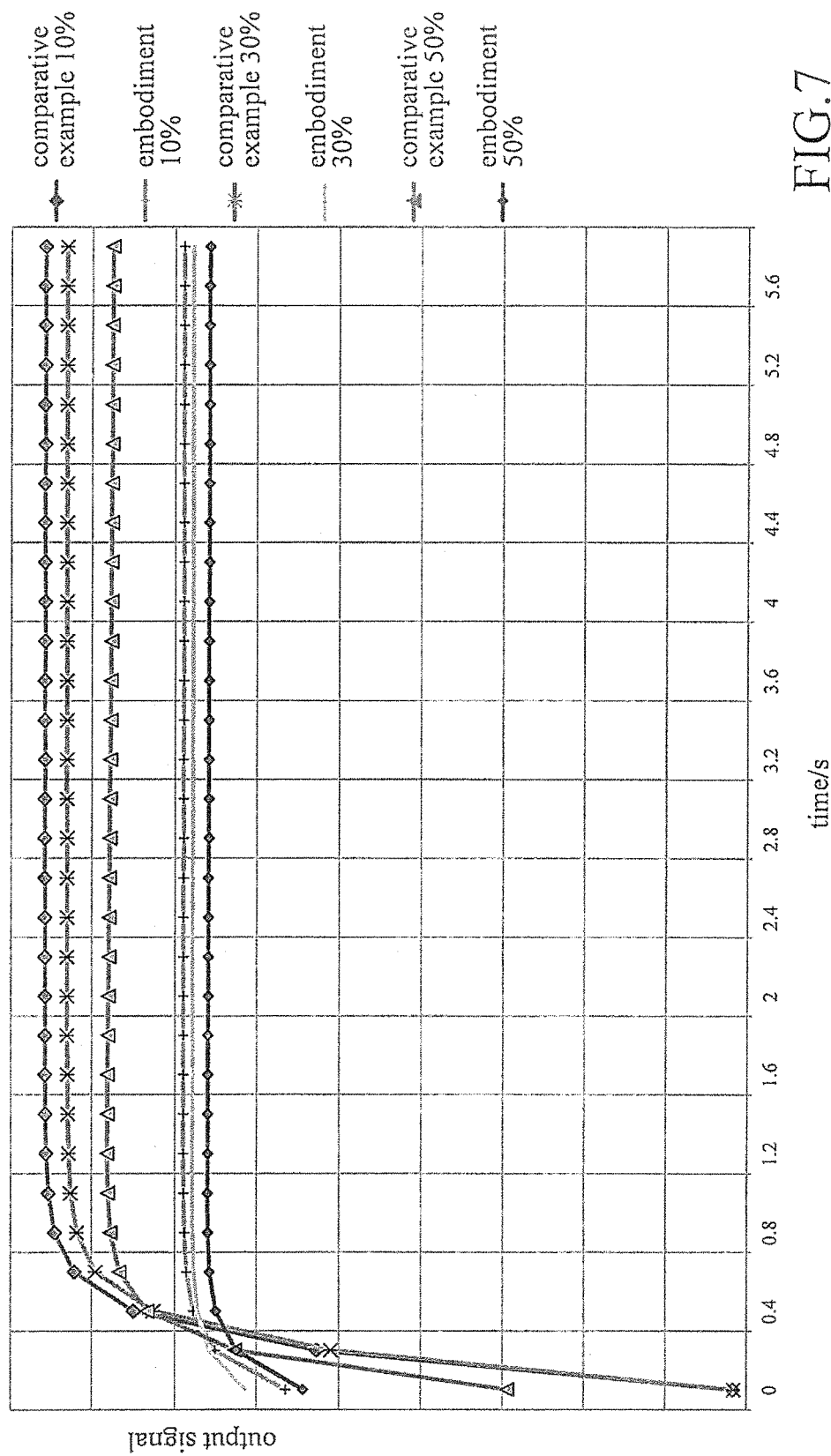
FIG. 7 schematically illustrates comparison results between the measured adjusted capacitor in parallel arrangement and the measurement apparatus without characteristic capacitance adjustor.

FIG. 7 schematically shows comparison results between the measured adjusted capacitor in parallel arrangement and the measurement apparatus without characteristic capacitance adjustor, illustrating the output signal-time relationship with respect to 10%, 30% and 50% of HCT concentration respectively. Referring to FIG. 7, as comparative examples, after inputting the measurement signal, a reaction begins occurring in the blood sample. Signals gradually rise to a steady state within at least 0.8 seconds. In contrast, the adjustment capacitor is in parallel with the blood sample of the present invention. When an electrochemical test strip is inserted into the measurement apparatus and starts a measuring process, energy storage has been proceeding with the adjustment capacitor. When the blood sample flows into the reaction zone of the electrochemical test strip, the adjustment capacitor starts to release energy until the blood sample begins to release the response signal which is superimposed on the energy released by the capacitor. The rise time of the response signal by the blood sample can thus be reduced within 0.4 seconds to a steady state, thereby with the effect of reducing the measurement time.

In FIGS. 6g-6k, the relationship between the adjusted capacitance of the capacitance characteristic adjustor and the capacitance of the blood sample is presented in series, such that the capacitance $C_{eq}$ of the overall circuit satisfies the following simplified equation:

$$1/C_{eq}=1/C_b+1/C_{ac} \quad (3)$$

The capacitors in series are equivalent to expanding the distance of capacitor electrode, thus reducing the overall capacitance. Surprisingly, though the overall capacitance of the circuit is reduced, electrical signal detected by the measurement apparatus is also reduced. Detected noises caused by the Na+/K+-ATPase and other components in the blood may also be reduced such that the HCT concentration may be easily analyzed by a calculation unit, thereby effectively reducing influence by other components in the blood.

In FIGS. 6l-6p, the relationship between the adjusted capacitance and the blood sample is presented in series and in parallel, such that the capacitance $C_{eq}$ of the overall circuit satisfies the following simplified equation:

$$C_{eq}=[(C_{C1}*C_b)/(C_{C1}+C_b)]+C_{C2} \quad (4)$$

When the capacitor is both in series and in parallel with the blood sample, the blood sample is in series with $C_{C1}$ so as to reduce noise caused by the Na+/K+-ATPase and other components in the blood. The capacitance value of overall circuit is then increase by $C_{C2}$, to facilitate capture of the signal by the calculation unit.

According to embodiments of the present invention, there is no limitation to the adjusted capacitance value of capacitance characteristics adjustor. The capacitance value, however, is limited to not affecting the capacitance properties of the blood sample. The capacitance value is preferable in a range of 1 pF-150 µF, more preferable in a range of 50 pF-20 µF.

In the following comparative examples, commercially available biological complex impedance measurement circuit is used with a carbon electrode and a metal electrode in measured HCT comparison with the electrochemical test strip of the present invention. The implementation steps are disclosed as follows:

1. Two biological complex impedance measurement circuits are respectively connected to a carbon electrode electrochemical test strip and a metal electrode electrochemical test strip. Then the measuring circuit of the present invention is connected to a carbon electrode electrochemical test strip of the same model and production batch.
2. The blood samples with various HCT concentrations were respectively placed and dripped onto the carbon electrode electrochemical test strip and the metal electrode electrochemical test strip.
3. Measurement signals of each circuit are retrieved within 30 seconds.
4. The above steps are repeated for five times.

By implementation of the abovementioned steps, the response signal curve of the HCT with each measurement apparatuses can be acquired. The response curve can be converted to a current signal by means of a backend operation circuit. The HCT measurement signal containing interfering signals may present in the results in each measurement apparatus due to reaction(s) caused by other components in the blood.

Figure 8:
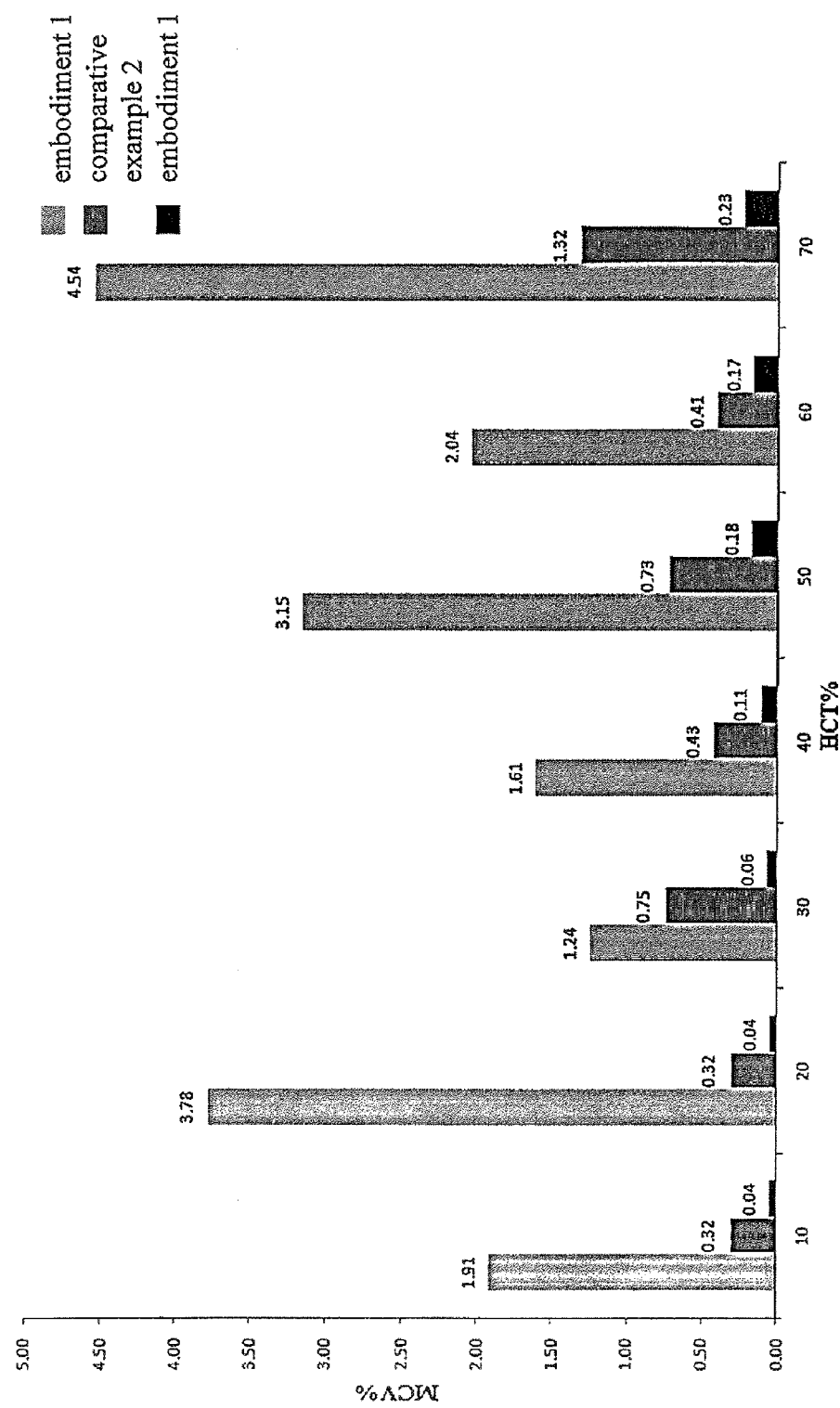
FIG. 8 shows the comparing results of the coefficient of variation (CV) of the output signals by each measurement apparatus.

FIG. 8 shows the comparing results of the coefficient of variation (CV) of the output signals by each measurement apparatus. Those skilled in the art generally appreciate that the coefficient of variation represents error to the measurement results. Referring to FIG. 8, a mean error of comparative example 1, in which a biological complex impedance measurement circuit is connected with a carbon electrode electrochemical test strip, is 2.6%. In comparative example 2, the biological complex impedance measurement circuit is in conjunction with a metal electrode electrochemical test strip. Due to excellent conductivity of the metal electrode, influence on impedance of the electrode can be prevented. The coefficient of variation of the metal electrode is smaller than that of the carbon electrode. For example, the coefficient of variation of the metal electrode is 0.6%. According to embodiment 1, interference to HCT measurements caused by other components in the blood can be effectively reduced due to provision of the capacitance characteristic adjustor. According to embodiments of the present invention, the average measuring error is only 0.12% in conjunction with a carbon electrode electrochemical test strip, and can be maintained at 0.1% level for 10% to 60% concentration of measurement, or the error can be even closer to 0.

Figure 9:
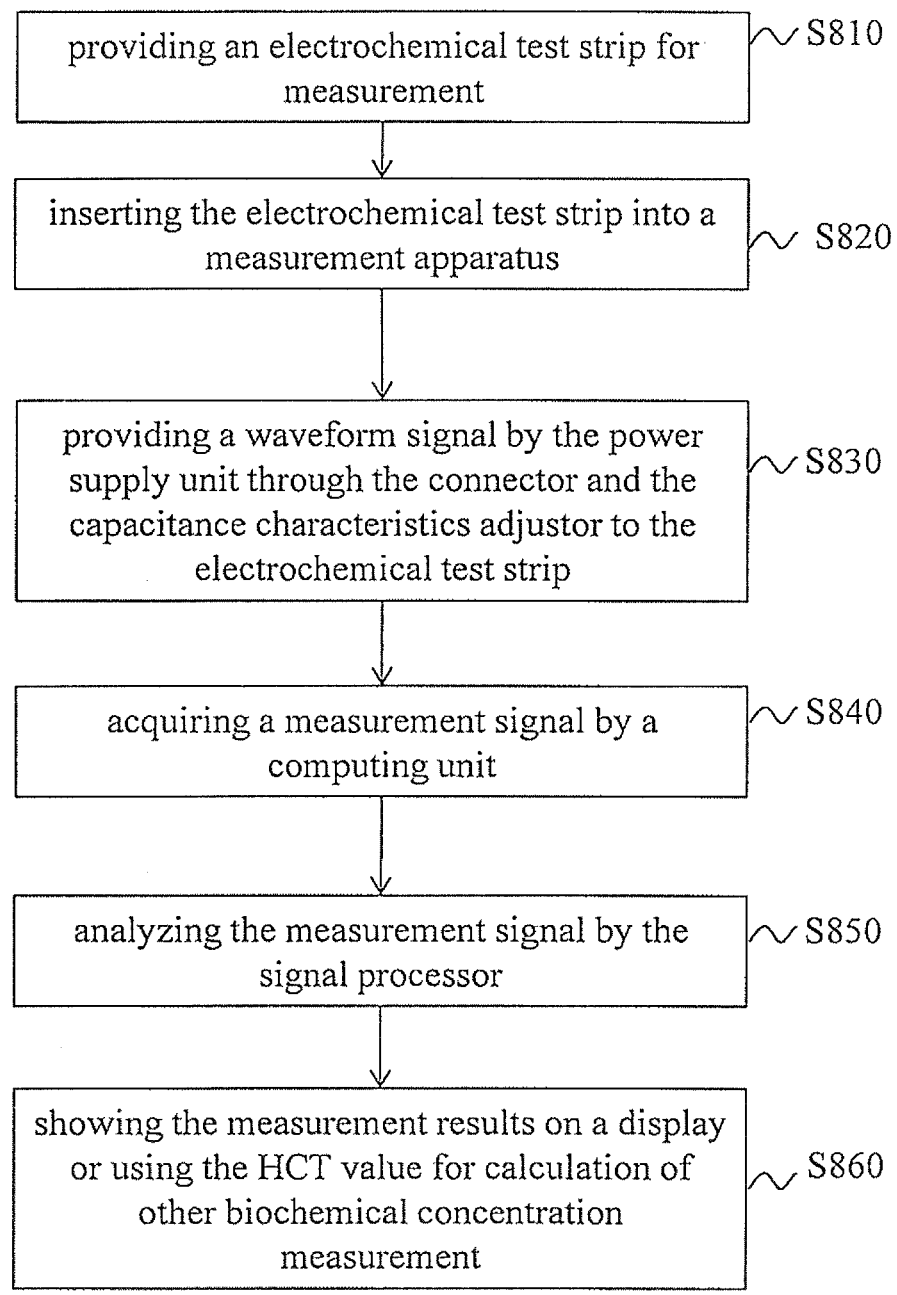
FIG. 9 is a flow chart illustrating a method for HCT measurement using the HCT measurement system of the present invention.

FIG. 9 is a flow chart illustrating a method for HCT measurement using the HCT measurement system of the present invention. First, an electrochemical test strip for measurement is provided (step S810). The electrochemical test strip may include, but is not limited to four electrodes insulated from each other: a working electrode, a reference electrode, a first electrode HCT measurement electrode and a second HCT measurement electrode, wherein the first and second HCT measurement electrodes are electrically connected to the measurement apparatus and the capacitance characteristic adjustor. As mentioned above, the adjusted capacitance of the capacitor characteristic adjustor and the blood sample are in series and/or in parallel relationship. Next, the electrochemical test strip is inserted into a measurement apparatus (step S820). The measurement apparatus can be started by the insert action or be started manually. After starting the measurement apparatus, a waveform signal is provided by the power supply unit through the connector and the capacitance characteristics adjustor to the electrochemical test strip (step S830). Subsequently, a measurement signal is acquired by a computing unit (step S840). For example, the signal of divided voltage can be measured by the measurement apparatus, and the signal processor of computing unit retrieves the signal on impedance of the voltage divider. Thereafter, the measurement signal is analyzed by the signal processor (step S850). The signal is digitized by an analog-digital converter and transmitted to the processor. The measurement results by the processor are shown on a display or the HCT value can be used for calculation of other biochemical concentration measurement (step S860). The digitized signal of the measurement results received by the processor can be directly displayed on a monitor, or other biochemical concentration can be calculated by means of the HCT value.

While the invention has been described by way of examples and in terms of preferred embodiments, it would be apparent to those skilled in the art to make various equivalent replacements, amendments and modifications in view of specification of the invention. Therefore, the scope of the appended claims should be accorded the broadest interpretation so as to encompass all such replacements, amendments and modifications without departing from the spirit and scope of the invention.

The invention claimed is:

1. A hematocrit (HCT) measurement system, comprising:
    an electrochemical test strip;
    a measurement apparatus comprising:
        a power generator providing a signal;
        a connector transmitting an initial signal generated from a blood sample to the measurement apparatus;
        a calculation unit for calculating concentration and HCT value of the blood sample respectively;
        an A/D convertor transforming the corresponding initial signal to a digital reacted signal; and
        a signal processor processing the digitalized reaction signal and showing measured results on a display; and
    a capacitive reactance adjustor disposed between the test strip and the measurement apparatus;
    wherein the capacitive reactance adjustor comprises a circuit consisting of a loading resistor and at least one adjusting capacitor.

2. The HCT measurement system as claimed in claim 1, wherein the calculation unit measures impedance signal so as to calculate the HCT value of the blood sample.

3. The HCT measurement system as claimed in claim 2, wherein a value of the impedance is approximately in a range of 200 Ω~2 MΩ.

4. The HCT measurement system as claimed in claim 1, wherein a waveform of the signal is a DC square wave signal with a frequency approximately in a range of 1 KHz~22 KHz and a voltage approximately in a range of 50 mV~5 V.

5. The HCT measurement system as claimed in claim 1, wherein the signal processor comprises an operational amplifier, an adder, a subtractor, an integrator, and a circuit consisting any combination thereof.

6. The HCT measurement system as claimed in claim 1, wherein the capacitance value of the adjusting capacitor is approximately in a range of 1 pF~150 uF.

7. The HCT measurement system as claimed in claim 6, wherein the adjusting capacitor of the capacitive reactance adjustor and a capacitance of the blood sample present a parallel relationship.

8. The HCT measurement system as claimed in claim 7, wherein an overall circuitry capacitance $C_{eq}$ of the signal processor satisfies the following equation:

$$C_{eq}=C_b+C_{ac},$$

where $C_{eq}$ is the overall circuitry capacitance, $C_b$ is the capacitance of the blood sample, and $C_{ac}$ is the adjusting capacitance.

9. The HCT measurement system as claimed in claim 6, wherein the adjusting capacitor of the capacitive reactance adjustor and a capacitance of the blood sample present a serial relationship.

10. The HCT measurement system as claimed in claim 9, wherein an overall circuitry capacitance $C_{eq}$ of the signal processor satisfies the following equation:

$$1/C_{eq}=1/C_b+1/C_{ac},$$

where $C_{eq}$ is the overall circuitry capacitance, $C_b$ is the capacitance of the blood sample, and $C_{ac}$ is the adjusting capacitance.

11. The HCT measurement system as claimed in claim 6, wherein the adjusting capacitor of the capacitive reactance adjustor and a capacitance of the blood sample present a relationship coexisting in serial and in parallel.

12. The HCT measurement system as claimed in claim 11, wherein an overall circuitry capacitance Ceq of the signal processor satisfies the following equation:

$$C_{eq}=[(C_{C1}*C_b)/(C_{C1}+C)]+C_{C2},$$

where $C_{eq}$ is the overall circuitry capacitance, $C_b$ is the capacitance of the blood sample, $C_{C1}$ is a serial adjusting capacitance and $C_{C2}$ is a parallel adjusting capacitance.

13. The HCT measurement system as claimed in claim 1, wherein the electrochemical test strip is equipped with an identification unit.

14. A method for measuring hematocrit (HCT) using an HCT measurement system, comprising:
providing an electrochemical test strip;
placing the electrochemical test strip into the HCT measurement system as claimed in claim 1;
providing a wave function signal to the electrochemical test strip transmitted from a power generator to the connector and the capacitive reactance adjustor;
acquiring a measuring signal through the calculation unit;
analyzing the measuring signal through the signal processor; and
showing a measured HCT value on a display through the signal processor or using the HCT value to calculate concentration of other biochemical.

15. The method as claimed in claim 14, wherein the step of acquiring a measuring signal through the calculation unit comprises measuring impedance by a measurement instrument to obtain the measuring signal.

* * * * *